US00PP08547P

United States Patent [19]

Gargiulo

[11] Patent Number: Plant 8,547

[45] Date of Patent: Jan. 18, 1994

[54] "JOLLY" GRAPEVINE

[75] Inventor: Angel A. Gargiulo, Mendoza, Argentina

[73] Assignees: Milan M. Caratan; Luis M. Caratan, both of Delano, Calif. ; a part interest

[21] Appl. No.: 31,871

[22] Filed: Mar. 16, 1993

[51] Int. Cl.[5] ..... A01H 5/00

[52] U.S. Cl. ..... Plt./47.1

[58] Field of Search ..... Plt. 47.1

*Primary Examiner*—James R. Feyrer

*Attorney, Agent, or Firm*—Worrel & Worrel

[57] ABSTRACT

A new and distinct variety of grapevine substantially as illustrated and described and which is distinguished principally as to novelty by producing intensely pink-red seedless berries with very good flavor and size forming loose bunches in which the berries are firmly attached to their capstems and being mature for harvesting and shipment approximately September 1 through September 15 in Delano in the San Joaquin Valley of California.

1 Drawing Sheet

BACKGROUND OF THE NEW VARIETY

The present invention relates to a new and distinct variety of grapevine which will hereinafter be denominated varietally as "Jolly" and, more particularly, to a grapevine which bears seedless berries which are of an intense pink-red coloration, have a very good flavor and size and which are mature for harvesting and shipment approximately September 1 through September 15 in Delano in the San Joaquin Valley of California.

The development of new commercial varieties of fruit is a science requiring diligent efforts over prolonged periods of time, keen powers of observation and considerable good fortune. The horticulturist must produce or select those varieties deemed worthy of further observation; plant them in a controlled environment for such further observation; painstakingly observe the plants through several growing seasons; faithfully record the individual characteristics of the new varieties frequently numbering in the thousands; compare the individual characteristics of the new varieties, one to another, through the several growing seasons; and ultimately select one or more of the varieties for further development.

Once the selection has been made, the varieties selected are asexually reproduced and, in a sense, the process begins anew. Each variety selected is observed over, usually, several growing seasons until it has borne one or more crops to confirm that those attributes which caused the parent variety to be selected are present in the progeny. While in the case of commercial fruit varieties it is the commercial appeal of the fruit which is a paramount concern, there are a myriad of other considerations which are also of importance and yet which may be significantly more difficult to detect unless observed over many years. For example, considerations such as resistance to pests and disease, hardiness, the shipping quality of the fruit, prolonged shelf life and the like are all factors to be evaluated.

With the advent of a world economy for commercial fruit varieties, another factor is becoming of increasing importance. While the potential commercial significance of having opposite seasons in the northern and southern hemispheres has long been recognized, this potential has only relatively recently begun to be realized. The increase in price which can be obtained for fruit counterbalances the cost of shipment making possible the potential for a virtually year around availability of many fruit varieties. However, since the market for fruit, as with most consumer products, is dependent upon educating the consumer to recognize and purchase particular varieties, there is considerable commercial advantage in developing commercial fruit varieties which have superior characteristics when grown in both the northern and southern hemispheres.

The new variety of grapevine of the present invention possesses a unique combination of attributes which make it a particularly promising variety in that it fits well with existing commercial varieties having ripening dates over substantially contiguous time periods and otherwise has exceptional characteristics in the above-noted respects, particularly in its superior characteristics both when grown in the northern and southern hemispheres.

ORIGIN AND ASEXUAL REPRODUCTION OF THE NEW VARIETY

The present variety of grapevine was discovered by the inventor as a hybrid of the "Lattuario Nero" grapevine, the "Cardinal" grapevine and the "Thompson Seedless" grapevine. The inventor produced the hybrid of the present invention in Vinedos y Bodegas Arizu S. A., Villa Atuel, San Rafael, Mendoza, Argentina in 1966. The grapevine of the present invention was asexually reproduced by the inventor at the same location in Argentina in 1969 and the same attributes observed in the parent were found precisely to have been duplicated in the progeny.

Subsequently, in 1986 another individual working in cooperation with the inventor asexually reproduced the grapevine of the new variety using green cuttings in mist propagation and lignified cuttings on the property located in Delano in the San Joaquin Valley of California. These grapevines of the new variety were also observed and the attributes of the parent were noted to have precisely been duplicated in the progeny with, of course, the single exception being the dates of flowering and maturity which are dependent upon the hemisphere in which they are grown. The asexually reproduced grapevines of the new variety have therefore been observed in both the northern and southern hemispheres and been confirmed faithfully to duplicate those characteristics hereafter set forth.

SUMMARY OF THE NEW VARIETY

The grapevine of the new variety is characterized as to novelty by producing high quality fruit having seedless, intensely pink-red berries which are of a very good size forming a bunch remaining loose with a firm attachment to the capstem. The fruit ripens for commercial harvesting approximately September 1 through September 15 in Delano in the San Joaquin Valley of California at least three weeks after the "Flame Seedless" grapevine. The variety is more vigorous in vine growth habit and slightly less productive than the "Flame Seedless" grapevine. Because of the tight attachment of the pedicel to the berry, there is very little berry shatter during and after harvest. This characteristic is an improvement over other commercial grape varieties resulting in improved shipment and retail shelf life.

BRIEF DESCRIPTION OF THE DRAWING

The accompanying drawing is a color photograph of the "Jolly" grapevine of the new variety showing selected representative bunches of grapes thereof sufficiently mature for harvesting and shipment, selected berries sectioned to show the flesh thereof and selected foliage, all of the new variety.

DETAILED DESCRIPTION

Referring more specifically to the pomological details of this new and distinct variety of grapevine, the following has been observed under the ecological conditions prevailing near Delano in the San Joaquin Valley of central California, except as otherwise noted. All major color code designations are by reference to the Dictionary of Color by Maerz and Paul, First Edition, copyright 1930. Common color names are also occasionally employed.

The following description was developed from clusters and plant material obtained from a test vineyard of the "Jolly" grapevine growing near Delano, Calif. The vines in the vineyard had been girdled and had received one application of gibberellic acid for fruit sizing, but not a second application of gibberellic acid for berry thinning.

VINE

Generally: Somewhat upright growing with long internodes and only a slight tendency to produce laterals. It is of average productivity on a spur pruned bilateral cordon system. With normal canopy, is minimally affected by sunburn caused by high temperatures.

*Vigor.*—Very vigorous.

*Growth.*—Vigorous in growth characteristics.

*Productivity.*—Medium. Slightly less productive than "Flame Seedless" grapevine. A cane system of pruning should be utilized for this variety in order to maximize productivity. Produces one cluster on most shoots; although, occasionally producing two clusters per shoot.

*Vine — size.*—Medium. About equal to the "Thompson Seedless" grapevine and more vigorous than the "Flame Seedless" grapevine.

Canes:

*Numbers.*—Depending on pruning style, a large number of canes are produced and some must be manually removed to avoid excessive shading.

*Diameter.*—10 mm (0.39 inches). An average size of 10 internodes at the middle third of 10 canes in September.

*Pattern of growth.*—Horizontal to semi erect.

*Color.*—Reddish Brown.

*Nodes — size.*—Enlarged.

*Tendrils — size.*—Average.

*Length.*—20 cm (7.87 inches). Average of 10 shoots at middle third of shoot at time flowering.

*Position.*—Normal for vinefera vine.

*Form.*—Long with typical vinifera branching pattern.

*Shape.*—Mostly trifurcated.

*Canes.*—Medium in thickness with a medium joint frequency of 15 cm (5.91 inches) to 20 cm (7.87 inches).

*Canes — form.*—Woody shoot cross section most frequently circular to slightly elliptic.

*Mature canes — color.*—Light cinnamon brown (12-F-8) with a very finely striated surface.

*Tendrils.*—Abundant and tendril distribution is most frequently discontinuous.

*Tendrils — form.*—Trifid, although bifid forms are occasionally present.

*Tendrils — length.*—Slender and moderately long for the most developed specimens; 20 cm (7.87 inches) to 28 cm (11.02 inches).

*Mature tendrils — color.*—Pale green-yellow (18-J-3).

*Tendrils — immature shoots.*—Reddish, especially basally. Spanish Cedar (6-J-10).

*Growing tips.*—Tip indument pubescent with a short wooly pubescence. Tips have a relatively strong anthocyanin intensity.

Trunk: Slender, straight.

*Bark.*—Tight clinging and generally smoother than the usual vinifera vine.

LEAVES

Size:

*Generally.*—Medium to large.

*Average length.*—Length ranges from 14.5 cm (5.71 inches) to 17.0 cm (6.69 inches) on large mature leaves from the petiolar junction to the apex of the center lobe.

*Average width.*—7 cm (2.75 inches).

Form: Mature leaves are pentagonal. Cuneate, some flat, others folded, mildly bullate—deeply five lobed. Lightly pubescent, more noticeable in the veins.

Surface texture:

*Upwardly disposed surface.*—Relatively smooth.

*Downwardly disposed surface.*—Smooth, lightly pubescent.

Upwardly disposed surface:

*Color.*—Dark green (24-L-4) with no anthocyanin coloration of the primary veins.

Downwardly disposed surface:

*Color.*—Lighter grey-green (22-L-5 Cerro Green) with primary vein color a light yellow-green (18-J-2). No anthocyanin coloration present on lower side of primary veins.

Leaf margin: Broadly serrate.

Petiole:

*Length.*—Long and variable from 14 cm (5.51 inches) to 20 cm (7.87 inches).

*Thickness.*—3.0 mm (0.118 inches) to 5.0 mm (0.197 inches).

*Color.*—Light green (18-I-6) and often tinged with red anthocyanin, especially near the petiolar attachment to the leaf blade.

Petiole sinus: Strikingly U-shaped.

Upper leaf sinuses: Closed with moderate overlapping of the lobes.

*Shape.*—Variable from a smooth U-shape to approaching a broad V-shape.

Lobes: Five with an open petiolar sinus.

Lobe apices:

*Form.*—Acute.

FLOWERS

Flowers:

*Type.*—Hermaphrodite.

*Date of bloom.*—Second week of May. Depending on temperature, lasts from 5 to 8 days.

*Stamens.*—Yellow, self fertile with upright stamens.

*Number.*—Five.

*Pollen.*—Heavy.

*Date of first bloom.*—1st of May in 1992 at Delano, Calif.

*Date of full bloom in 1992.*—May 7. The new variety is approximately one week later in bloom than "Thompson Seedless" grapevine and 14 days later than "Flame Seedless" grapevine.

*Floral cluster.*—Moderately narrow and tapering and of medium length. The first floral cluster occurs on the third to fifth joint. The cluster are below average in abundance.

*Floral cluster — length.*—At bloom range from 20 mm (0.787 inches) to 25 mm (0.984 inches) from peduncle to tendril and from 22 mm (0.866 inches) to 28 mm (1.10 inches) from tendril to the first rachis branch.

*Total floral cluster — length.*—Averages from 16.5 cm (6.50 inches) to 20.0 cm (7.87 inches).

*Total floral cluster — width.*—4.5 cm (1.77 inches) to 6.0 cm (2.36 inches). The flowers are hermaphroditic with moderately long stamens and average size anthers. The calyptra most frequently separates completely from the base.

*Pollen.*—Normal and abundant.

*Length of blooming season.*—Approximately 10 days.

*Cluster — color.*—Light green (19-K-6 Sea Green).

*Calyptra — color.*—Light green (19-K-7) before bloom.

FRUIT

Maturity when described: Ripe for commercial harvesting and shipment approximately September 1 through September 15 in Delano in the San Joaquin Valley of California. However, in 1992, onset of harvest was July 28 at Delano, Calif. with peak maturity by August 10. 1992 is believed to be an atypical year as it was for most other crops. In San Rafael, Mendoza, Argentina, the new variety ripens for commercial harvesting and shipment approximately March 1.

Cluster:

*Size.*—Medium to large. 20 cm (7.87 inches) by 15 cm (5.91 inches).

*Bunch density.*—Bunches are loose in density with some visible pedicels.

*Average number of berries in cluster.*—95. Large bunches have from 110 to 135 berries.

*Average cluster weight.*—Averages 1.5 lbs.

*Cluster shape.*—Somewhat conical with smaller than average shoulders.

*Peduncle — length.*—3 cm (1.18 inches).

*Peduncle — thickness.*—5 mm (0.20 inches).

Brush: Medium tensile strength to separate. Small amount of brush remain on pedicle.

Berry:

*Generally.*—Quite uniform within individual cluster.

*Berry shape.*—Slightly variable from globose to broadly elliptic in lateral aspect. Berry cross section quite globose.

*Berry — size.*—Diameter 2.36 cm (0.93 inches).

*Berry color — generally.*—Intense pink to red.

*Skin — color.*—Somewhat variable, depending on bunch exposure. Ranges from a maroon red (7-J-6 Garnet Red) to a lighter rose-red (5-H-4). Usually the lighter color shading is present over the stem end of the berry with light hues of green tint occasionally present. Medium density of greyish bloom is present over the berry surface. Berries are well colored even in areas moderately shaded by the leaf canopy.

*Texture.*—Light with no distinctive taste.

*Thickness.*—Medium thick.

*Bloom.*—Medium.

*Tendency to crack.*—None.

*Pedicel.*—Medium to slightly shorter than average, ranging from 9 mm (0.354 inches) to 12 mm (0.472 inches). Pedicel is well attached to the berry with very little shatter occurring even at advanced maturity.

*Pedicel — color.*—Medium green (19-G-9).

Flesh:

*Texture.*—Firm and crisp.

*Color.*—Variable from red (6-L-8 Dark Cardinal) to pink-red (5-K-7) with occasional light hues of green-yellow.

*Juice production.*—Colorless. Juicy.

*Flavor.*—Sweet with moderate acidity.

*Aroma.*—Slight, pleasant.

*Ripening.*—Even.

Seeds: Seedless. Two to three undeveloped, rudimentary soft seed traces often present.

Overall quality: Very good.

Storage quality: Maintains bright color. Stems do not dry or discolor quickly. No drying of fruit in storage.

Shipping quality: Maintains quality, does not bruise or discolor during shipping.

Eating quality: Very good.

Use: Fresh table grapes. A high quality seedless red skinned grape variety with excellent appearance and flavor, suited for use as a table grape for fresh consumption.

Resistance to disease: Good rot resistance, but variety has not been grown in California long enough to check resistance or susceptibility to rot for any length of time.

Although the new variety of grapevine possesses the described characteristics noted above as a result of the growing conditions prevailing near San Rafael, Argentina, except as otherwise noted, it is to be understood that variations of the usual magnitude and characteristics incident to changes in growing conditions, irrigation, fertilization, pruning, pest control and the like are to be expected.

Having thus described and illustrated my new variety of grapevine, what I claim as new and desire to be secured by Plant Letters Patent is:

1. A new and distinct variety of grapevine substantially as illustrated and described and which is distinguished principally as to novelty by producing intensely pink-red seedless berries with very good flavor and size forming loose bunches in which the berries are firmly attached to their capstems and being mature for harvesting and shipment approximately September 1 to September 15 in Delano in the San Joaquin Valley of California.

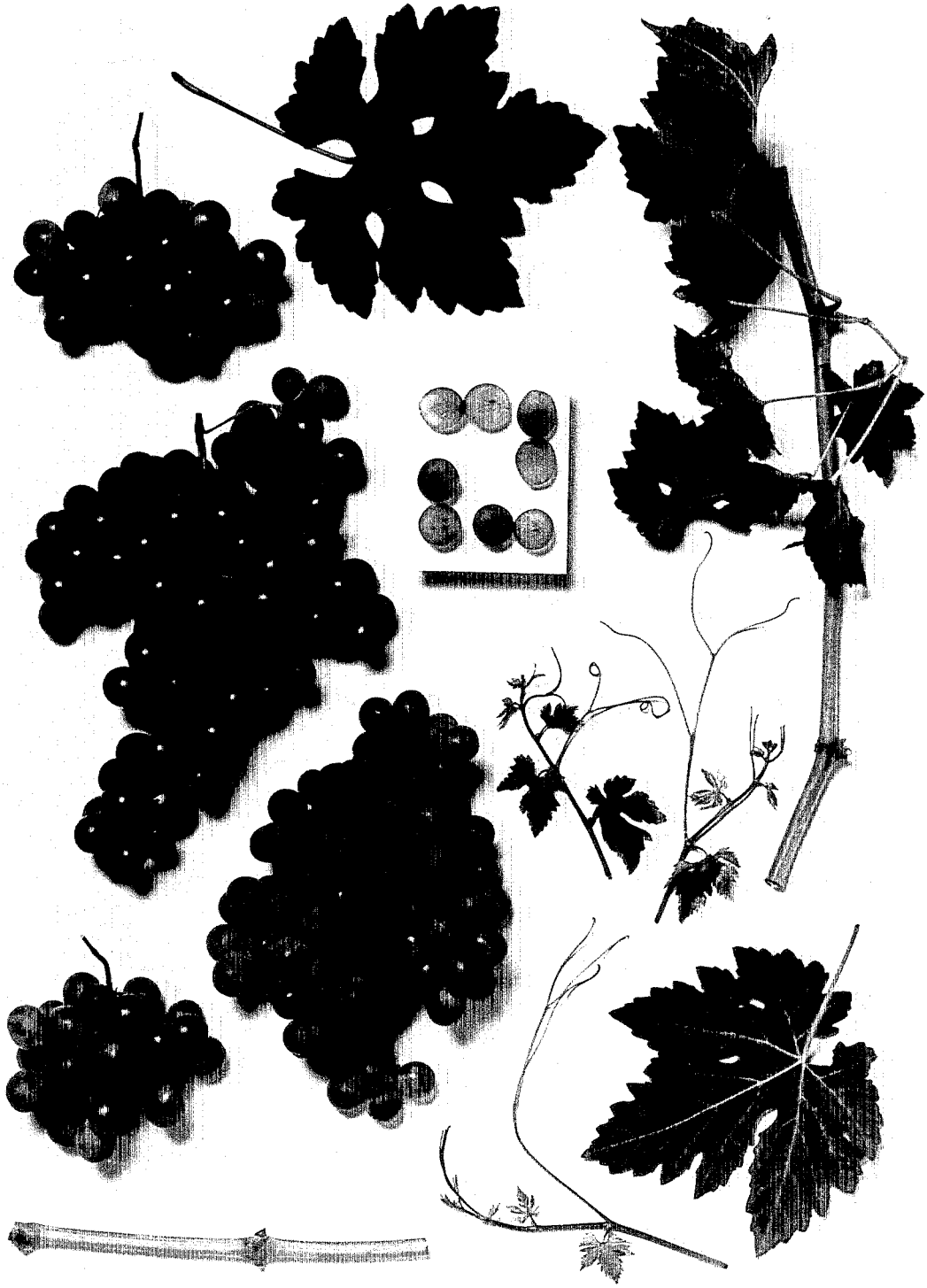

* * * * *